United States Patent
Mann, III et al.

(10) Patent No.: US 11,123,220 B1
(45) Date of Patent: Sep. 21, 2021

(54) GAS DELIVERY SYSTEM FOR CRYOCHAMBER

(71) Applicant: CryoXcel, LLC, Auburn, AL (US)

(72) Inventors: John H Mann, III, Auburn, AL (US); Roy J Hartfield, Jr., Auburn, AL (US)

(73) Assignee: CryoXcel, LLC, Auburn, AL (US)

( * ) Notice: Subject to any disclaimer, the term of this patent is extended or adjusted under 35 U.S.C. 154(b) by 0 days.

(21) Appl. No.: 16/198,717

(22) Filed: Nov. 21, 2018

Related U.S. Application Data

(60) Provisional application No. 62/589,304, filed on Nov. 21, 2017.

(51) Int. Cl.
*A61F 7/00* (2006.01)

(52) U.S. Cl.
CPC ...... *A61F 7/0053* (2013.01); *A61F 2007/006* (2013.01); *A61F 2007/0063* (2013.01)

(58) Field of Classification Search
CPC ........ A61F 2007/006; A61F 2007/0063; A61F 2007/0064; A61F 7/0053
See application file for complete search history.

(56) References Cited

U.S. PATENT DOCUMENTS

| | | |
|---|---|---|
| 3,591,962 A | 7/1971 | Connell |
| 3,650,290 A | 3/1972 | Moen et al. |
| 3,782,128 A | 1/1974 | Hampton et al. |
| 3,807,396 A | 4/1974 | Fischel |
| 4,838,270 A * | 6/1989 | Donnerhack ......... A61F 7/0053 128/DIG. 27 |
| 4,918,927 A | 4/1990 | Eigenbrod |
| | (Continued) | |

FOREIGN PATENT DOCUMENTS

GB    1160245    8/1969

OTHER PUBLICATIONS http:/cryocabins.se/what-is-whole-body-cryo-therapy/; screenshot obtained from the world wide web on Mar. 28, 2019; Mar. 28, 2019.
(Continued)

*Primary Examiner* — Allen Porter
*Assistant Examiner* — Adreanne A. Arnold
(74) *Attorney, Agent, or Firm* — Jonathan C. Hill; Jake M. Gipson; Bradley Arant Boult Cummings LLP

(57) ABSTRACT

An improved gas delivery system for a cryochamber that increases the efficiency, efficacy, and safety of cryotherapy treatments is disclosed. The system incorporates a high pressure cryogenic liquid source and a plurality of fluid discharge orifices for conveying fluid into the chamber. The orifices may further comprise atomizing nozzles, which eliminate the need for a heater in the system. The orifices are dispersed about the chamber and positioned to convey fluid either clockwise or counterclockwise about a central vertical axis of the chamber to promote cyclonic gas motion. The cryochamber may further comprise shielding that reduces the risks associated with inadvertent liquid discharge. The orifices may also be positioned at varying heights in the chamber and have varying diameters to facilitate targeted cryotherapy treatments. The improved gas delivery system enables the cryochamber to achieve the same or improved therapeutic benefits while consuming less cryogenic liquid per treatment and less energy.

23 Claims, 10 Drawing Sheets

(56) References Cited

U.S. PATENT DOCUMENTS

| | | | |
|---|---|---|---|
| 5,131,440 A | 7/1992 | Quinn | |
| 5,174,122 A | 12/1992 | Levine | |
| 5,573,532 A * | 11/1996 | Chang | A61B 18/02 228/221 |
| 5,855,322 A | 1/1999 | Py | |
| 6,226,996 B1 * | 5/2001 | Weber | A61B 18/0218 236/51 |
| 6,513,521 B1 | 2/2003 | Gier et al. | |
| 6,730,236 B2 | 5/2004 | Kouba | |
| 6,880,350 B2 | 4/2005 | Tilton | |
| 10,271,986 B1 * | 4/2019 | Guertin | A61F 7/0053 |
| 2002/0074674 A1 * | 6/2002 | Keeney | F24F 6/14 261/116 |
| 2003/0199866 A1 * | 10/2003 | Stern | A61F 7/007 606/41 |
| 2005/0004635 A1 * | 1/2005 | Brojek | A61F 7/0053 607/104 |
| 2014/0276792 A1 | 9/2014 | Kaveckis | |
| 2015/0033765 A1 | 2/2015 | Blalock | |
| 2017/0007443 A1 | 1/2017 | Stroze et al. | |
| 2017/0209302 A1 * | 7/2017 | Yliollitervo | A61F 7/0053 |
| 2019/0151140 A1 * | 5/2019 | Trembley | A61F 7/0053 |

OTHER PUBLICATIONS http://titancryo.com; screenshot obtained from the world wide web on Mar. 28, 2019 Mar. 28, 2019.

https://space-cabin.com/products/; screenshot obtained from the world wide web on Mar. 28, 2019 Mar. 28, 2019.

https://www.cryoinnovations.com/; screenshot obtained from the world wide web Mar. 28, 2019 Mar. 28, 2019.

https://www.youtube.com/watch?v=E1McVXC6sec; Video from around time of Super Bowl 51, which was Feb. 2017 Mar. 28, 2019.

Impact Cryotherapy, Product information sheets related to Cryotherapy; 6 pages; obtained around Oct. 2016.

Spraying Co., Product Specification Sheets for Hydraulic Atomizing Nozzles; 4 pages; obtained from Spraying Systems on Sep. 21, 2018.

* cited by examiner

GAS DELIVERY SYSTEM FOR CRYOCHAMBER

CROSS REFERENCE TO RELATED APPLICATIONS

This application claims the benefit of and priority to U.S. Provisional Application No. 62/589,304, filed on Nov. 21, 2017, and entitled "Gas Delivery System for Cryochamber," the disclosure of which is expressly incorporated by reference in its entirety.

FIELD OF INVENTION

This disclosure relates to devices for providing cryotherapy and more particularly to whole-body cryotherapy chambers and their gas delivery systems.

BACKGROUND

Whole-body cryotherapy is becoming more popular to treat various ailments. Most systems consist of a cryotherapy machine (a cryochamber) that has an internal patient chamber. In most cases, the internal patient chamber is dimensioned to contain a standing adult from approximately his shoulders down. The chamber is usually open at the top so that the client stands with his head above the chamber. The patient chamber is chilled by cryogenic gases, which are generated using a cryogenic liquid source connected to the cryochamber. In operation, the patient chamber is cooled well-below freezing, with an exemplary target temperature being approximately −230° F. (−110° C.). An exemplary cryotherapy treatment consists of a client standing in the cooled chamber for one to a few minutes.

The basic components of a typical cryotherapy system are as follows. A low pressure source of cryogenic liquid (such as a tank filled with liquid nitrogen) is in fluid communication with a valve or regulator. The valve or regulator may control the discharge of fluid from the source or may regulate the pressure output from the source. The valve or regulator is in fluid communication with a heater. The heater is usually electrically powered and warms the cryogenic liquid passing through the heater so that the liquid vaporizes into cryogenic gas. The heater is in fluid communication with one or more solenoid valves, which receive the warmed fluid from the heater. Each of the solenoid valves are in fluid communication with, and control the flow of cryogenic fluid to, one or more low pressure jets. The low pressure jets are disposed in a cryochamber and discharge the cryogenic fluid into the chamber to cool it.

Key challenges exist with achieving the therapeutic benefits of cryotherapy treatment in a cost-effective, safe, and beneficial way. The therapeutic benefit of cryotherapy is derived from the ability of the device to achieve a short period of very high heat transfer rates between the extremely cold gas of the cryochamber and the skin of a client. The success of devices to date has depended on conduction to transfer heat from a client's skin to essentially stagnant gas in the patient chamber. Although this approach will cool the client's skin, it can require high consumption rates of cryogenic liquid to maintain the patient chamber at a sufficiently low temperature throughout the treatment. The use of cold, stagnant gas generally means that the entire chamber must be cooled to the desired temperature even though the therapeutic effects are usually most desirable on certain parts of the body, such as around a client's core or torso. Thus, uniform cooling may be wasteful because the extreme temperatures are not desirable or therapeutic for certain parts of the client's body, such as the feet, which are typically protected by clothing or outerwear during the treatment. Further, to ensure that the cooling effect sufficiently penetrates the client's skin, the chamber may sometimes be kept at colder temperatures or clients may be treated for longer periods of time.

One of the leading concerns for cryotherapy treatment is the risk of exposing the client's skin to the cryogenic liquid associated with cooling the cryochamber. Such exposure can produce burns that can be extremely harmful to the client. To avoid this risk, cryotherapy machines are ordinarily designed to convert the cryogenic liquid into a cryogenic gas before injecting the cryogenic fluid into the patient chamber. That design is conventionally considered to be less dangerous to a client. As a result, most cryochambers have various features, like heaters, to encourage the liquid to convert to a gas before the fluid is discharged into the cryochamber. In other words, the devices are designed for the cryogenic liquid to experience its phase change before entering the patient chamber. Despite these features, small amounts of cryogenic liquid sometimes reach the chamber. These features also yield inefficiencies. In particular, heaters (or other devices that promote phase change) are inefficient because, in spite of the objective of cooling the chamber, the heater warms the liquid and converts it to a gas before any fluid is dispersed into the chamber. This process increases the amount of cryogenic liquid required to cool the chamber because the thermal energy of the cryogenic fluid is intentionally increased before the fluid reaches the chamber. It also increases the energy consumption of the cryochamber because considerable energy is required to operate the heater.

A need therefore exists for a cryochamber having an improved gas delivery system that increases the efficiency, efficacy, and safety of cryotherapy treatments. Advantageously, the improved gas delivery system will promote higher or more efficient heat transfer rates and may allow for targeting the cryotherapy treatment at certain regions of a client's body. These features will allow patients to achieve the same or improved therapeutic benefits while consuming less cryogenic liquid per treatment. Preferably, the improved gas delivery system will also improve the efficiency of the cryochamber by delivering cryogenic fluid to the chamber without the need to warm or increase the thermal energy of the cryogenic fluid. More preferably, the improved gas delivery system will disperse cryogenic fluid in a manner that reduces the likelihood of inadvertent discharge of cryogenic liquid, and optionally, the cryochamber may also protect clients from any cryogenic liquid that is inadvertently discharged. It is also preferable that the improved gas delivery system disperse cryogenic fluid about the chamber in a manner that promotes heat transfer between the client's skin and the air in the chamber.

SUMMARY OF THE INVENTION

This disclosure describes an improved cryochamber having an improved gas delivery system. Advantageously, embodiments of the improved cryochamber produce a highly effective thermal energy transfer environment by promoting a cyclonic gas motion inside the patient chamber. The cyclone or vortex effect increases the rate of heat transfer from a client's skin to the air in the chamber because heat is transferred by both conduction and convection. Optionally, the chilled gases associated with the vortex may be focused on particular regions of the cryotherapy machine so that particular areas of a client's body are targeted for the therapeutic benefits. Preferably, embodiments of the improved cryochamber also deliver cryogenic fluids to the patient chamber without the need to heat or otherwise increase the thermal energy of the cryogenic fluid before dispersion into the chamber. Advantageously, the improved gas delivery system ensures that cryogenic liquid is rapidly and efficiently converted into cryogenic gas, thereby protecting clients from harmful exposure. Optionally, embodiments may also include features to protect clients from inadvertent discharge of cryogenic liquid. Embodiments of the invention may satisfy one or more, but not necessarily all, of the needs and capabilities discussed throughout this disclosure.

In a first embodiment, a cryotherapy chamber is provided and comprises a plurality of walls forming a patient chamber; and a plurality of fluid discharge orifices disposed about the patient chamber, wherein at least two of the orifices are positioned to discharge cryogenic fluid in a clockwise or a counter-clockwise direction about a central vertical axis of the patient chamber.

In a second embodiment, a heaterless cryotherapy system is provided and comprises a plurality of walls forming a patient chamber; a fluid input adapted to receive a cryogenic liquid; and a plurality of atomizing nozzles disposed about the patient chamber and in fluid communication with the fluid input to receive the cryogenic liquid at a discharge pressure, wherein the plurality of atomizing nozzles are operable at the discharge pressure to discharge atomized cryogenic liquid into the patient chamber.

In a third embodiment, a heaterless cryotherapy system is provided and comprises a high pressure cryogenic liquid source capable of supplying a cryogenic liquid at a supply pressure of at least about 50 psi; a plurality of walls forming a patient chamber; and a plurality of atomizing nozzles disposed about the patient chamber and in fluid communication with the source to receive the cryogenic liquid at a discharge pressure of at least about 50 psi, wherein the plurality of atomizing nozzles are operable to discharge atomized cryogenic liquid into the patient chamber.

In a fourth embodiment, a cryotherapy chamber is provided and comprises a plurality of walls forming a patient chamber; and a plurality of fluid discharge orifices disposed about the patient chamber, wherein a first fluid discharge orifice is located at a first height in the patient chamber and has a first flow rate, wherein a second fluid discharge orifice is located at a second height in the patient chamber and has a second flow rate, and wherein the first height is different from the second height and the first flow rate is greater than the second flow rate.

The above summary presents a simplified summary to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

The following drawings are attached to and form a portion of this disclosure.

DEFINITIONS

Figure 1:
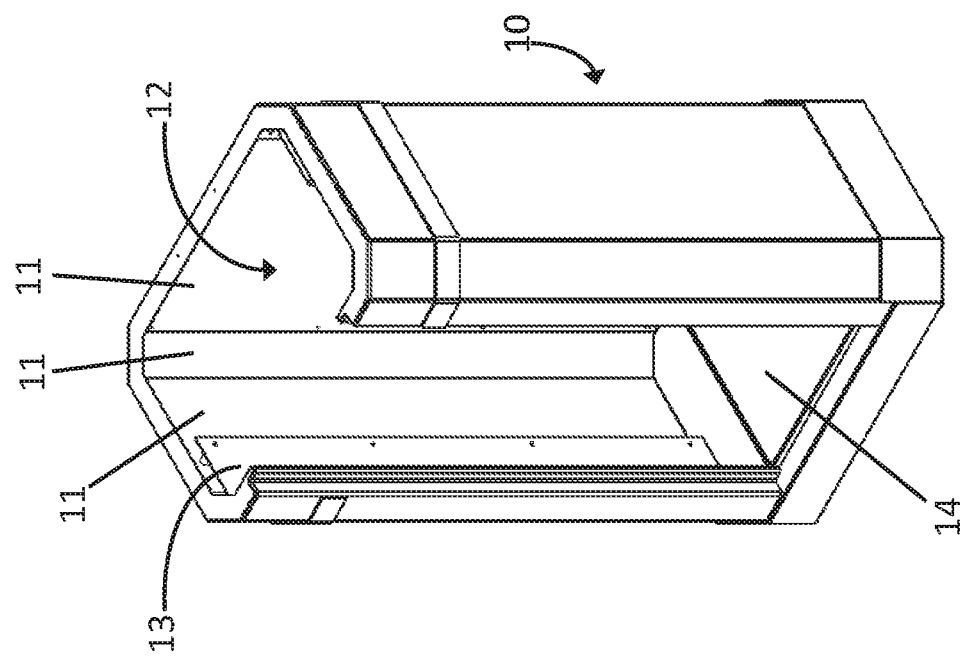
FIG. 1: A perspective view of one embodiment of the cryochamber with the door removed.
Figure 2:
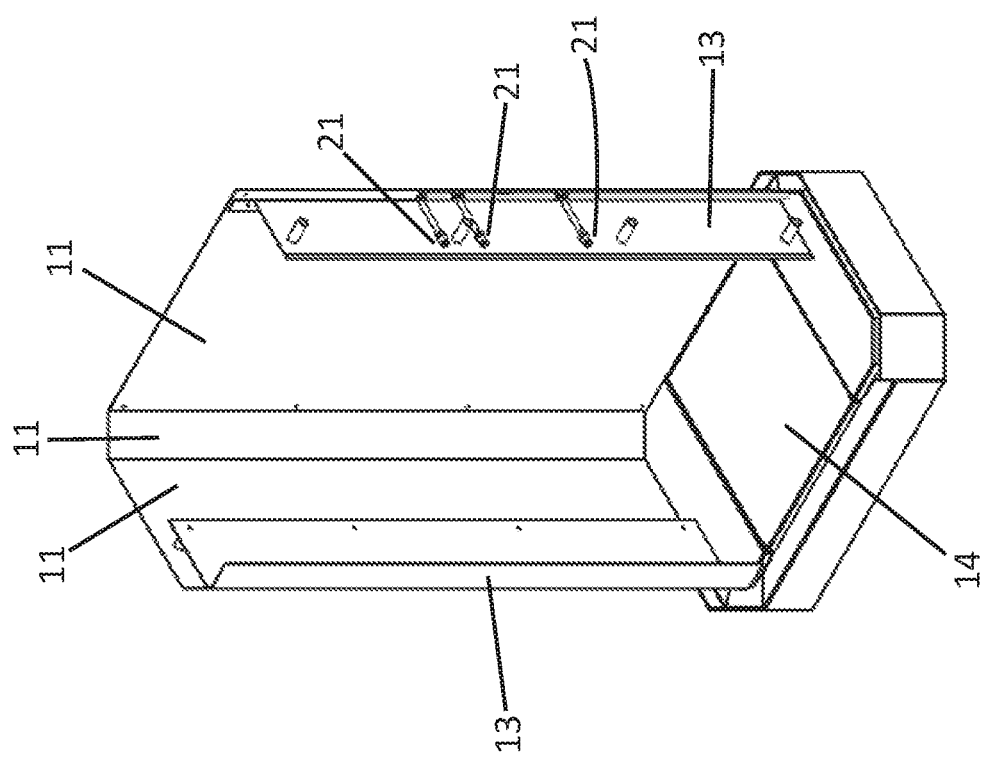
FIG. 2: A perspective view of one embodiment of the cryochamber with the exterior walls and some interior walls removed to expose some of the piping and nozzles.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well-known functions or constructions may not be described in detail for brevity or clarity.

The terms "about" and "approximately" shall generally mean an acceptable degree of error or variation for the quantity measured in the light of the nature or precision of the measurements. Typical, exemplary degrees of error or variation are within 20 percent (%), preferably within 10%, and more preferably within 5% of a given value or range of values. Numerical quantities given in this description are approximate unless stated otherwise, meaning that the term "about" or "approximately" can be inferred when not expressly stated.

The terminology used herein is for the purpose of describing particular embodiments only and is not intended to be limiting. As used herein, the singular forms "a", "an," and "the" are intended to include the plural forms as well, unless the context clearly indicates otherwise.

The terms "first," "second," and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure. Likewise, terms like "top" and "bottom" or "front" and "back" are used to distinguish certain features or elements from each other, but it is expressly contemplated that a top could be a bottom, and vice versa.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. This term excludes such other elements that adversely affect the operability of what is claimed for its intended purpose as stated in this disclosure, even if such other elements might enhance the operability of what is claimed for some other purpose.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The following description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational cues. These headings shall not limit or characterize the invention(s) set forth herein.

DETAILED DESCRIPTION

Various embodiments of an improved cryochamber and an improved gas delivery system for cryochambers have been developed and are described in this disclosure. Referring to the figures and drawings, we generally discuss a whole-body cryotherapy machine with a top-open patient chamber that is designed for a patient to stand in the chamber with his head above the opening. The teachings and improvements described in this disclosure, however, are not limited to such embodiments. As will be understood by one of ordinary skill in the art, some or all of the teachings in this disclosure may be advantageous to various cryotherapy techniques. Non-limiting examples of other uses include enclosed whole-body cryotherapy machines and localized cryotherapy machines. Such variations are expressly contemplated as within the scope of this disclosure.

Embodiments of Gas Delivery Systems Promoting Vortex Effects

One embodiment of the cryochamber and gas delivery system is depicted in FIGS. 1 through 6. In this embodiment, the cryochamber 10 comprises a plurality of walls 11 that form a patient chamber 12 and a plurality of fluid discharge orifices 21 spaced around the plurality of walls 11. Each fluid discharge orifice 21 is preferably positioned to disperse gas approximately parallel to the tangent of the wall 11 nearest the orifice 21, and preferably every orifice 21 discharges its gas in either the same essentially clockwise direction or the same essentially counter-clockwise direction. Optionally, at least one shield 13 extends along one of the plurality of walls 11, and one or more of the plurality of fluid discharge orifices 21 are disposed between the shield 13 and the wall 11.

In operation, this structure enables a more efficient heat transfer and, thus, a more efficient cryotherapy chamber. As cryogenic gas is fed into the patient chamber 12 using the plurality of fluid discharge orifices 21, the gas is dispersed approximately parallel to the tangent to the walls 11 of the chamber. Because each orifice 21 discharges the gas in the same direction (either clockwise or counter-clockwise about a vertical axis running through the center of the patient chamber 12), a cyclonic cold gas motion, or swirl, is promoted within the chamber. That swirl or vortex in turn increases the heat transfer rates within the patient chamber 12. The orientation of the orifices 21 also simultaneously protects a client from inadvertent discharge of cryogenic liquid because the orifices 21 are aimed along and substantially parallel to the walls 11 (and thus not in the direction of the client standing in the center of the chamber). If the chamber also incorporates shields 13 extending along the walls 11, the client is further protected from any inadvertent discharge of cryogenic liquid that occurs from an orifice 21 positioned in the narrow passageway between the shield 13 and the wall 11. In sum, embodiments of this improved gas delivery system for a cryochamber produces a highly effective thermal energy transfer environment while robustly protecting the client from droplets of cryogenic liquid.

These components, their operation, and numerous variations of this embodiment are now described in greater detail.

The walls 11 may be constructed from any suitable material. In an exemplary embodiment, the walls 11 are metallic and may be surrounded by or filled with an insulator. Other materials or combinations of materials may also be used instead (e.g. glass, fiberglass, plastics, etc.), and any known structure for constructing cryochambers may be used. One or more of the plurality of walls 11 may be formed by a door (not shown) of the cryochamber 10. The door, which allows ingress and egress of a client in the chamber, has been removed from the figures to show the interior detail of the cryochamber.

Preferably, the walls 11 are arranged in a shape that promotes the cyclonic cold gas motion (also described as the whirl or vortex effect) associated with the fluid discharged into the patient chamber 12. Generally speaking, the preferred shapes for this purpose are walls 11 that are curved or meet at obtuse angles rather than walls 11 meeting at right or sharp angles. In an exemplary embodiment, the walls 11 forming the patient chamber 12 have a horizontal cross section that is essentially a circular or ovular shape. In other embodiments, such as that shown in FIGS. 3 and 4, the patient chamber 12 may have a horizontal cross section that is essentially an octagon shape or essentially a rectangular shape. In embodiments with essentially a rectangular shape, the walls 11 may include various features, such as rounded or chamfered corners, to promote the cyclonic effect of the circulating gas.

A plurality of fluid discharge orifices 21 are disposed about the patient chamber 12 and spaced around the plurality of walls 11. The fluid discharge orifices 21 may be any suitable nozzle, jet, or other opening in a pipe that is suitable for handling and discharging cryogenic fluids. In an exemplary embodiment, the fluid discharge orifices 21 are high speed jets and, preferably, atomizing nozzles. More particularly, as described in one preferred embodiment below, the orifices may be hydraulic atomizing nozzles. Other examples of suitable jets include a spiral cone nozzle and a mister nozzle.

Each orifice 21 is positioned adjacent to one of the walls 11. As used herein, adjacent to means near or proximate to a wall 11 but not necessarily adjoining or touching the wall 11. Each orifice is preferably within less than about 3 inches of the wall 11, more preferably within less than about 2 inches of the wall 11, and even more preferably within less than about 1 inch. In embodiments where the orifice is disposed between a wall 11 and a shield 13, the orifice is preferably disposed about half way between the wall 11 and the shield 13.

In preferred embodiments, each orifice 21 is oriented to discharge gas in a direction that is approximately parallel to a tangent of the nearby wall. In other words, if the nearest wall 11 is flat, the orifice 21 is oriented to discharge gas approximately parallel to the wall 11. But if the wall 11 is curved, the orifice 21 is oriented to discharge gas approximately parallel to a nearby tangent of the wall 11. Preferably, the orifice is oriented to discharge gas in a direction that is no more than 15°, more preferably no more than 10°, and even more preferable no more than 5° offset from the tangent. In other embodiments, however, none of the orifices 21 or less than all of the orifices 21 are oriented to discharge gas in a direction that is approximately parallel to a tangent of a nearby wall 11. For example, in some embodiments, one or more of the orifices may be oriented to discharge gas at an angle relative to the wall (for example, at an angle of about 20°, about 30°, or about 45°). Although the gas discharged in such designs will lose some of its velocity due to the gas stream colliding with the wall, such an orientation may still produce a whirl or vortex around the chamber.

Figure 3:
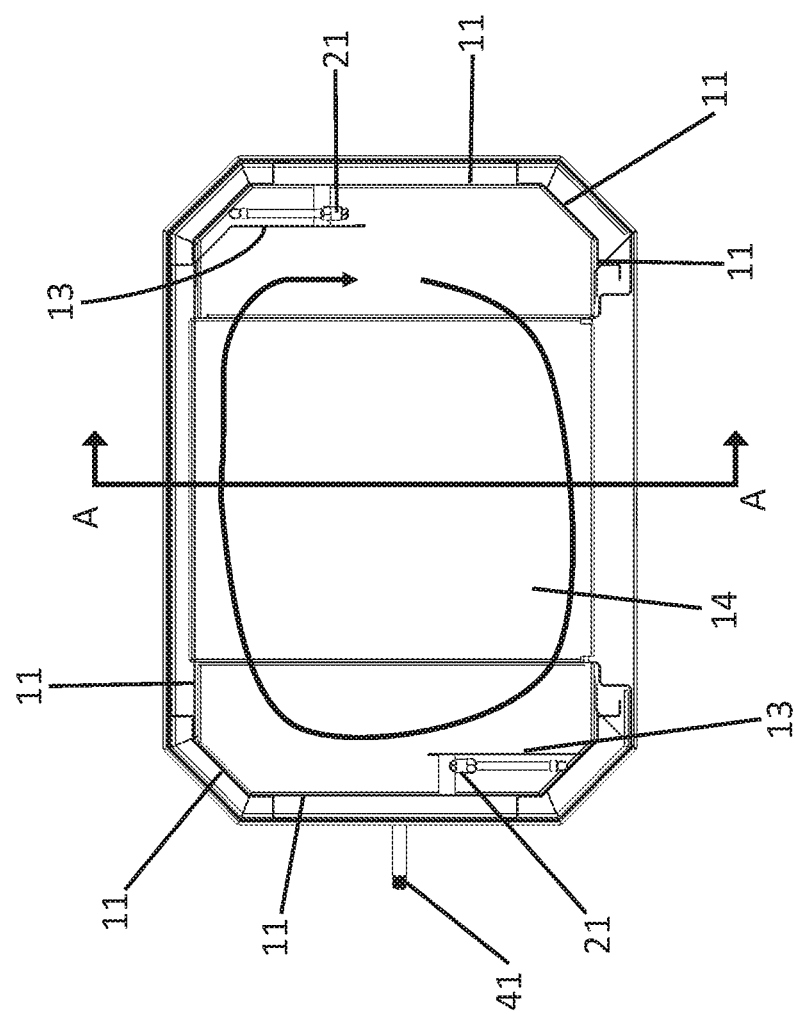
FIG. 3: A top view of one embodiment of the cryochamber with an arrow depicting the direction of circulation of gas within the chamber.
Figure 5:
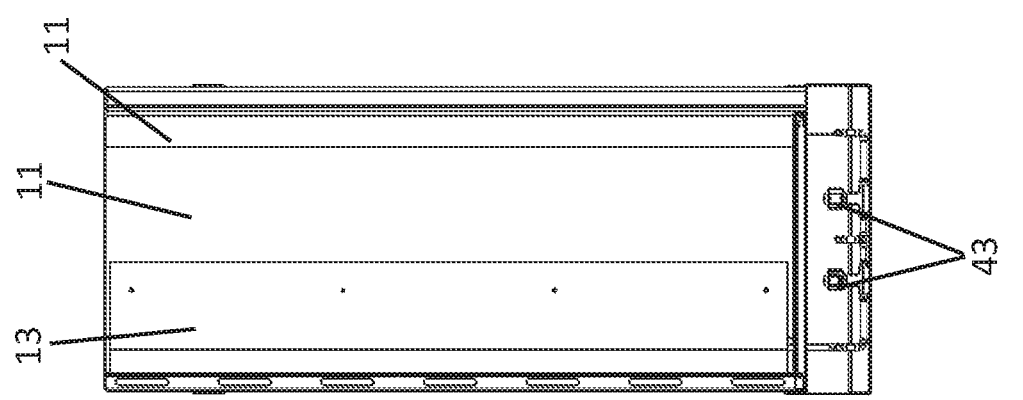
FIG. 5: A cross sectional side view, taken along line A shown in FIG. 3, of one embodiment of the cryochamber.
Figure 6:
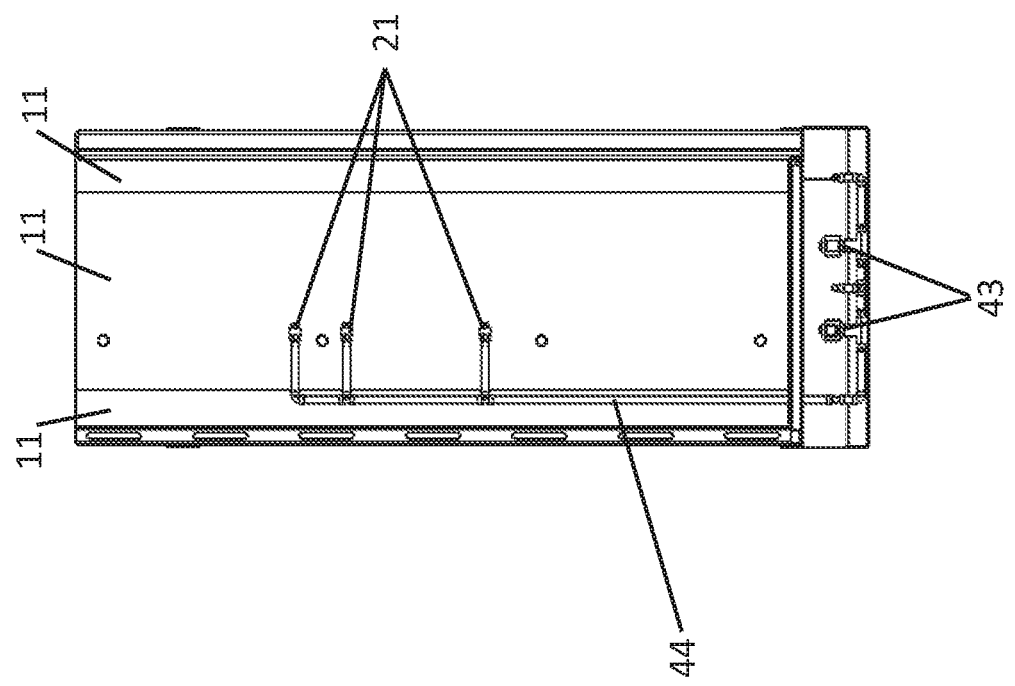
FIG. 6: A cross sectional side view, taken along line A shown in FIG. 3, of one embodiment of the cryochamber with the shielding removed to expose the piping and nozzles.

Preferably, two or more (but not necessarily all) of the orifices are also rotationally aligned with each other. As used herein, the term "rotationally aligned" means that the orifices discharge their gas in the same two-dimensional direction of rotation—either clockwise or counter-clockwise about the chamber—as viewed from above the patient chamber 12. FIG. 3 depicts an embodiment where the orifices 21 produce an clockwise rotation about a central vertical axis of the patient chamber, and the direction of rotation is denoted in the figure by an arrow. In other words, if an imaginary vertical axis is drawn through the center of the patient chamber, every orifice that is rotationally aligned would discharge in the same direction, either essentially clockwise or essentially counter-clockwise. The specific rotational direction, whether clockwise or counter-clockwise, is generally unimportant. Further, it should be understood that rotationally aligned does not imply or require that the orifices also discharge their gases in a strictly horizontal direction or in a direction that has a uniform vertical component to the direction. In some embodiments, such as shown in FIGS. 5 and 6, all of the orifices may be rotationally aligned to discharge in a strictly horizontal direction (i.e. no upward or downward directionality to the discharge). But in other embodiments, the orifices 21 may be rotationally aligned with one or more of the orifices oriented to discharge gas in a partially upward (or downward) direction to promote an upward (or downward) draft of the cryogenic gases. Optionally, in that same embodiment, some of the other orifices may be aligned in a partially downward direction to promote circulation toward the base of the patient chamber, and other orifices may be aligned horizontally (with no upward or downward directionality).

Figure 4:
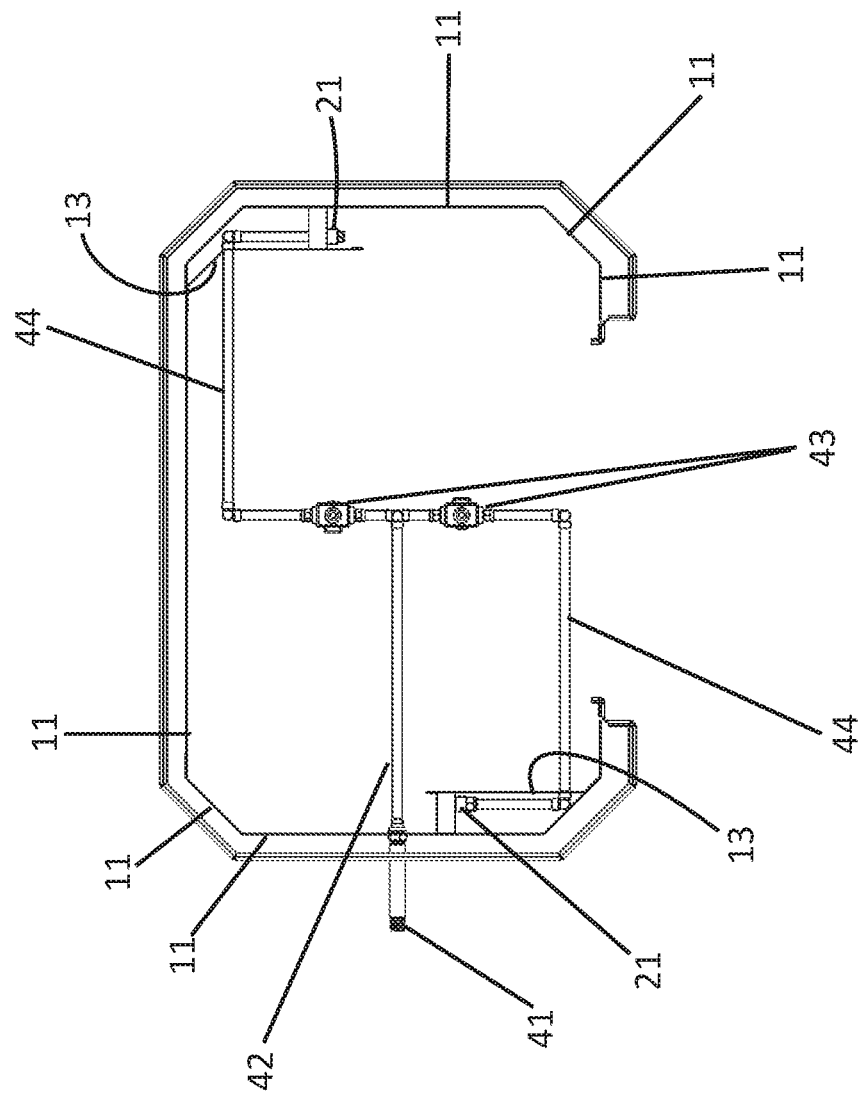
FIG. 4: A top view of one embodiment of the cryochamber with the floor of the patient chamber removed to expose some of the piping.
Figure 8:
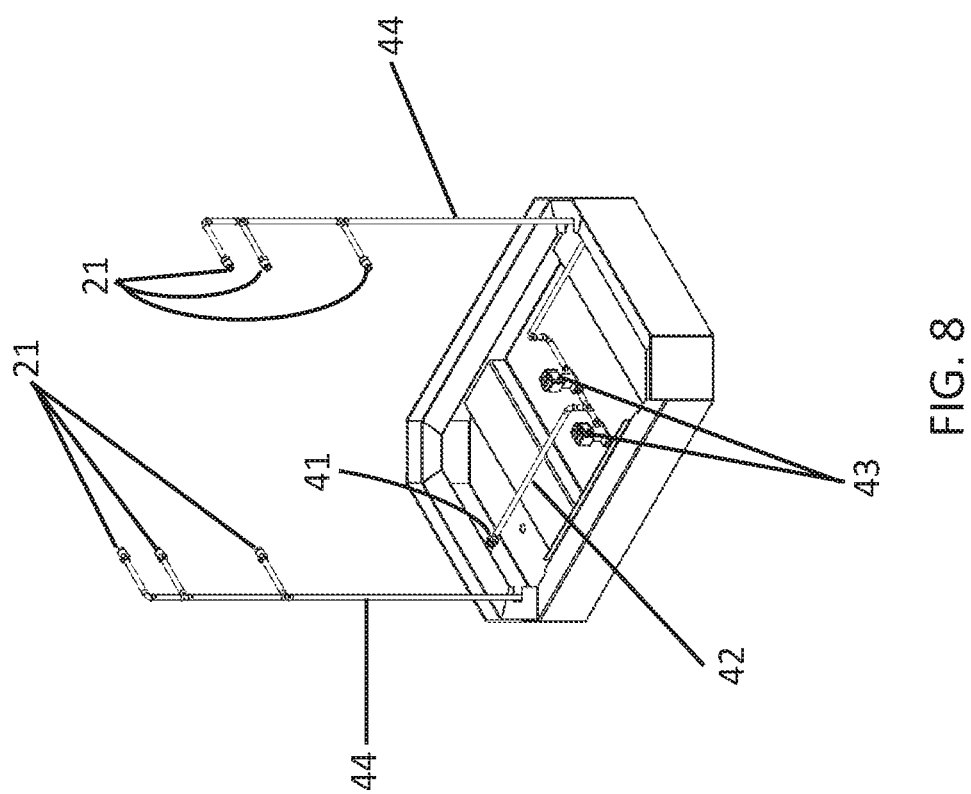
FIG. 8: A perspective view of one embodiment of the cryochamber with the exterior and interior walls removed to expose the piping and six nozzles of the embodiment.

The orifices 21 are in fluid communication with a source of cryogenic fluid (not shown). Any known and suitable method may be used for placing the orifices 21 in fluid communication with the source of cryogenic liquid. In the exemplary embodiment shown in FIGS. 4, 6, and 8, a series of pipes (or tubing) and solenoids fluidly connect the orifices to the cryogenic fluid source. More particularly, the connection to the cryogenic fluid source may comprise a fluid input 41 that is attached to a first length of piping 42 and is configured to couple (such as by threading) to the cryogenic fluid source. At least one solenoid 43 may be in fluid communication with the first length of piping 42. A second length of piping 44 is in fluid communication with the solenoid 43 and with one or more orifices 21. The solenoid 43 is operable to control the amount of fluid, if any, that is communicated to the associated orifices 21. The piping and orifices extending from the solenoid 43 are sometimes referred to as a delivery tree. As shown in FIG. 4, two or more solenoids 43 may be used to control different sets of orifices 21 (and delivery trees), such as orifices on opposing or different sides of the patient chamber. Embodiments may have one, two, three, four, or more delivery trees, with varying numbers of orifices per each tree, distributed about the patient chamber 12.

The piping, tubing, or other fluid carrying medium that joins the various components may be any that is suitable for use with the applicable cryogenic liquid and associated pressure. For instance, in one embodiment, the fluid carrying medium comprises stainless steel piping with a diameter of about ½ inch extending from the cryogenic liquid source, brass piping with a diameter of about ⅜ inches extending between the stainless steel piping and the solenoid(s), and copper piping with a diameter of about ¼ inch extending between the solenoid(s) and the fluid discharge orifices. In a preferred embodiment, the solenoid is powered by a 12 volt direct current, and more preferably, is capable of handling high pressure cryogenic liquid.

Embodiments may include any number of orifices 21, from as few as one or two orifices to as many as twenty or more orifices. In a preferred embodiment, there are between two and ten orifices, and more preferably between four and eight orifices 21, which are preferably spread among two to four delivery trees. Preferably, the plurality of orifices and delivery trees are dispersed around the plurality of walls, both in terms of height of individual orifices on the wall and the location of the trees and orifices along the perimeter (when viewed from above) of the chamber. In other words, the orifices are distributed so that not all of the orifices are located at the same height and so that not all of the orifices are located at the same location along the perimeter. Preferably, the orifices 21 are distributed at heights between about 10 inches and about 60 inches from the floor 14 of the patient chamber, and more preferably between about 20 inches and about 40 inches from the floor 14. Alternatively, in some embodiments it may be advantageous to distribute the height of the orifices with reference to the body of an average client. For instance, on or more orifices may be located at any combination of ankle height, shin height, knee height, thigh height, waist height, stomach height, chest height, and shoulder height. Preferably, the orifices are also distributed so that, if there are two delivery trees, they are located on two opposing walls or so that, if there are more than two delivery trees, the trees (and orifices) are spread roughly equidistantly along the perimeter.

An exemplary configuration of orifices is provided in FIGS. 2-4, 6, and 8. The embodiment comprises six fluid discharge orifices 21 that are divided between two delivery trees. Each delivery tree comprises three orifices 21 that are distributed at three different heights along the wall. As shown, the two delivery trees are located on opposing walls of the patient chamber 12. This configuration thus has the advantage that it promotes more uniform, yet targeted, distribution of gas and enhances the cyclone or vortex effect within the patient chamber 12. Depending on location, the varying heights of the orifices may help distribute the circulation of air throughout the height of the chamber or may focus the vortex effect at certain regions of the chamber. Having the orifices located on opposing walls also more uniformly distributes the strength of the cyclone or vortex around the chamber (as compared to if the orifices were located on only one wall). Preferably, the orifices on each delivery tree are spaced so that the top pair of orifices are around the height of a client's chest (e.g. at a height between about 44 inches and about 62 inches above the floor), the middle pair of orifices are around the height of a client's abdomen (e.g. at a height between about 34 inches and about 48 inches above the floor), and the bottom pair of orifices around the height of a client's knees (e.g. at a height between about 12 inches and about 24 inches above the floor).

The vortex or cyclone effect generated by the foregoing embodiments improves the thermal shock benefit of cryotherapy by more uniformly cooling the skin due to convection as a heat transfer mechanism. Convection occurs through bulk motion of the gas, which is driven by the orifice placement and the shape of the chamber. As compared to heat transfer occurring only through conduction, convection dramatically enhances the heat transfer rate. (A parallel analogy is wind chill. By flowing gas over a solid surface at substantial velocity, the thermal energy conducted into the gas from the article is swept away and lower temperature gas replaces the heated gas that was swept away. Thus, the maximum available thermal gradient is maintained between the surrounding air and the article, which allows the maximum amount of thermal energy to be continually conducted out of the article, thereby enhancing the heat transfer rate.) The end result is that, if all other variables are the same (including time and temperature of the treatment), a client may achieve greater therapeutic effects due to deeper or more uniform penetration of the cold temperatures into a client's body. Conversely, because of the windchill effect, convection may allow a client to achieve the same therapeutic benefits in a shorter period of time or in warmer environment than if the device operated based on energy transfer through only conduction.

In some embodiments, the cryochamber also incorporates one or more shields to direct the gas about the chamber and to protect the client during operation. A shield extends along one (or more) of the walls 11 for at least the length of the fluid discharge orifice 21 plus a short distance beyond the end of the fluid discharge orifice 21. Thus, the shield forms a channel XX that contains one or more of the fluid discharge orifices. The shield may span the entire or almost the entire height of the chamber or only a portion of its height. Advantageously, each shield forms a channel that directs the gas emanating from the orifice to travel between the shield and wall, and it also forms a barrier that protects the client from any cryogenic fluid that is inadvertently discharged. Even if cryogenic fluid is discharged from the orifices in this channel, any droplets expelled from the orifices would contact a surface (and thereafter vaporize) instead of striking the client. In general, the farther that the shield extends beyond the end of the orifice, the longer the resulting channel and the greater the protection for the client.

Optionally, the shield(s) may be removable, which allows for ease of cleaning and maintenance of the device. In some instances, each shield attaches to one or more walls 11, or in other instances, the shield extends from one of the walls 11. The shield may also be secured by other means to the cryochamber, for instance by securing the shield to the floor 14 or an upper portion of the cryochamber.

One embodiment having shields is depicted in FIGS. 1-5. As shown, the embodiment comprises two separate delivery trees of fluid discharge orifices, each of which is protected by a shield that extends almost the entire height of the chamber. Each shield is removably secured to at least two walls using a plurality of screws or other removable fasteners. Each shield extends along the wall and beyond the end of the fluid discharge orifice. Preferably, the shield extends at least 1 inch beyond the end of the fluid discharge orifice, and more preferably at least 3 inches beyond the end of the orifice.

High Pressure Gas Delivery System for Cryochambers

Figure 7:
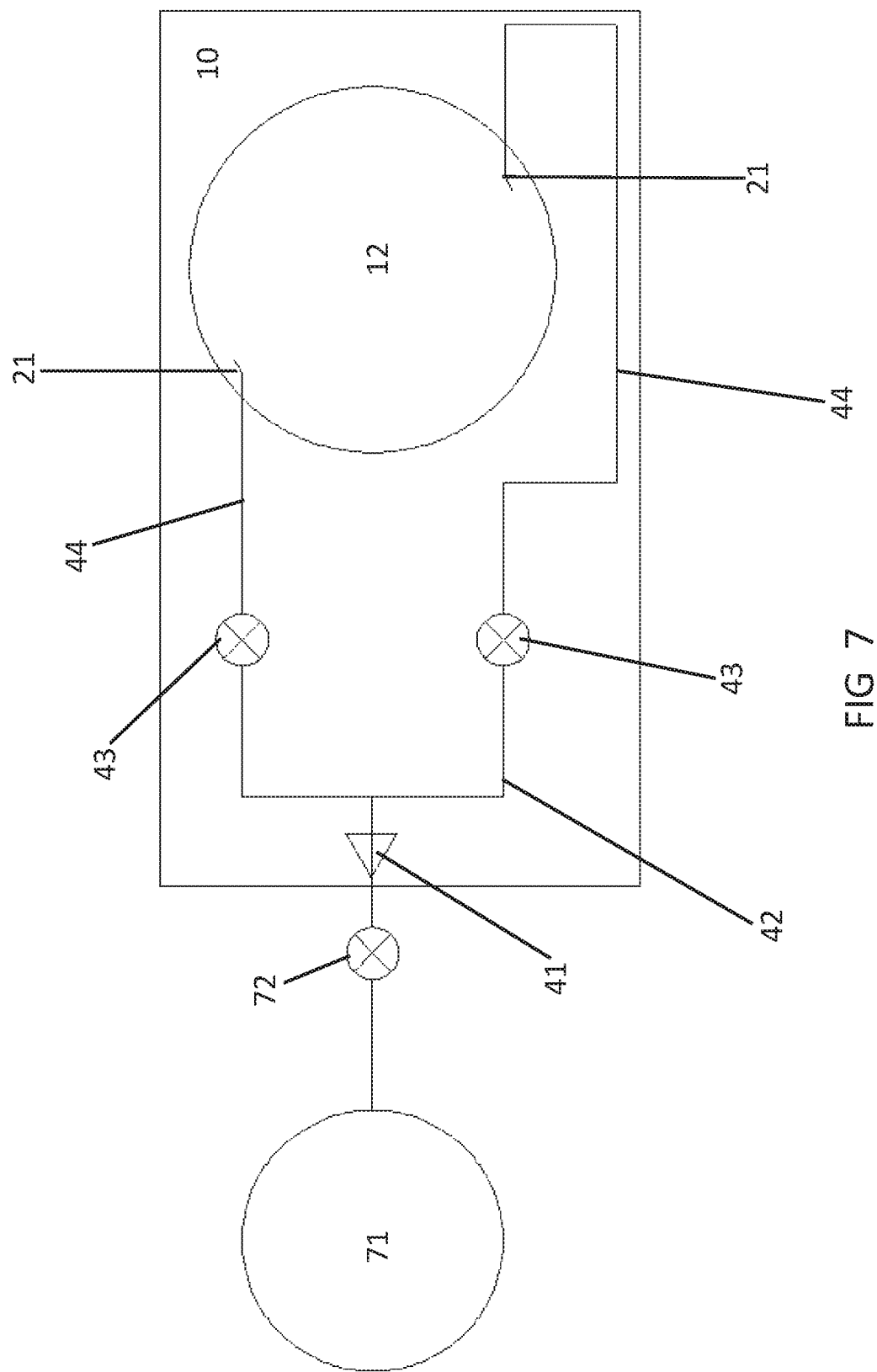
FIG. 7: A block diagram of one embodiment of the cryochamber.

Another embodiment of the cryochamber and gas delivery system is depicted in the block diagram of FIG. 7. In this embodiment, the cryochamber 10 has a fluid input 41 that is capable of connecting to and placing the cryochamber in fluid communication with a source of high pressure cryogenic liquid 71. In an exemplary embodiment, the source 71 contains cryogenic liquid stored at a pressure of approximately 200 psi. Optionally, one or more valves or regulators 72 may be disposed in the fluid communication pathway between the source of cryogenic fluid 71 and the fluid input 41. The fluid input 41 is in fluid communication with one or more solenoids 43, and each solenoid 43 is in fluid communication with one or more fluid discharge orifices 21 disposed in the patient chamber 12. By this configuration, the fluid discharge orifices 21 are therefore configured to discharge cryogenic fluid into the chamber at high pressures, preferably at a pressure of at least 100 psi.

This high pressure gas delivery system is advantageous in multiple respects. Provided that the cryogenic liquid is delivered to the fluid discharge orifice at a sufficiently high pressure and that an appropriate fluid discharge orifice is selected, the cryogenic liquid will atomize when the orifice disperses it into the patient chamber. The atomization is a result of the expansion pressure gradient and the shear action associated with the high velocities at which an appropriate fluid discharge orifice discharges the cryogenic liquid. Once the cryogenic liquid is atomized and exposed to the ambient atmosphere of the patient chamber, the liquid rapidly vaporizes into cryogenic gas. Advantageously, the vaporization of the liquid inside of the patient chamber enhances cooling of the chamber because the atomized cryogenic liquid draws the latent heat for vaporization from the atmosphere of the chamber (instead of a heater or another source). The patient chamber is therefore cooled by both the vaporization process and the temperature of the cryogenic gas. As a result, less cryogenic liquid is used to cool the chamber, and the cryochamber consumes less electricity due to the absence of a heater. Further, because the cryogenic liquid is atomized, it immediately vaporizes when entering the chamber. Accordingly, there is minimal risk that a client's skin will be exposed to harmful cryogenic liquid.

Embodiments of the high pressure gas delivery system are now explained in greater detail. It is expressly contemplated that embodiments of the high pressure gas delivery system may advantageously include the various features that promote a vortex effect, which are discussed in the embodiments above. Non-limiting examples of such combinations are sometimes mentioned below.

The cryogenic fluid source 71 may be a suitable source of a cryogenic liquid stored at high pressure. In an exemplary embodiment, the source 71 is a storage tank filled with liquid nitrogen at a pressure between about 180 psi and about 230 psi, and more preferably at a pressure of about 200 psi. More generally, the source 71 may contain any suitable cryogenic liquid stored at a high pressure. Such high pressure is preferably at least about 50 psi, more preferably at least about 80 psi, even more preferably at least about 100 psi, even more preferably at least about 150 psi, and even more preferably at least about 200 psi. The storage tank may be any suitable size, and in some embodiments the tank has a capacity between about 180 liters and about 230 liters. Alternatively, the storage tank may be any variety of microbulk tank, which may have a capacity of 1,000 liters or more. The cryogenic fluid source 71 may also comprise a source of cryogenic liquid stored at a lower pressure but that is supplied to the cryochamber 10 at a higher pressure through a pressure builder valve or another device that increases the pressure of the cryogenic liquid.

Optionally, at least one valve or regulator 72 is in fluid communication with and controls the discharge of fluid from the source 71. Examples of suitable valves include a globe valve and a gate valve, either of which may be mechanically or electrically operated. A pressure regulator may also be used instead of or in addition to a valve. The valve or regulator 72 may be operated to control the flow or the pressure of the liquid that is supplied to the cryochamber from the source 71. Some embodiments may also include one or more high pressure relief valves (not shown), with an example being a valve that releases pressure if the system exceeds 300 psi.

As discussed above, the fluid input 41 of the cryochamber may be any suitable fitting for placing the cryochamber in fluid communication with the source 71. In an exemplary embodiment, the fluid input 41 comprises a threaded pipe that is connectable to a correspondingly threaded pipe or fitting that is connected to the source 71.

The solenoid 43 may be any suitable solenoid that is capable of handling the pressures at which the cryogenic liquid travels through the system. Each solenoid 43 is selectively operable to allow or to stop the flow of cryogenic liquid to the one or more fluid discharge orifices 21 that are in fluid communication with the solenoid 43.

Figure 10:
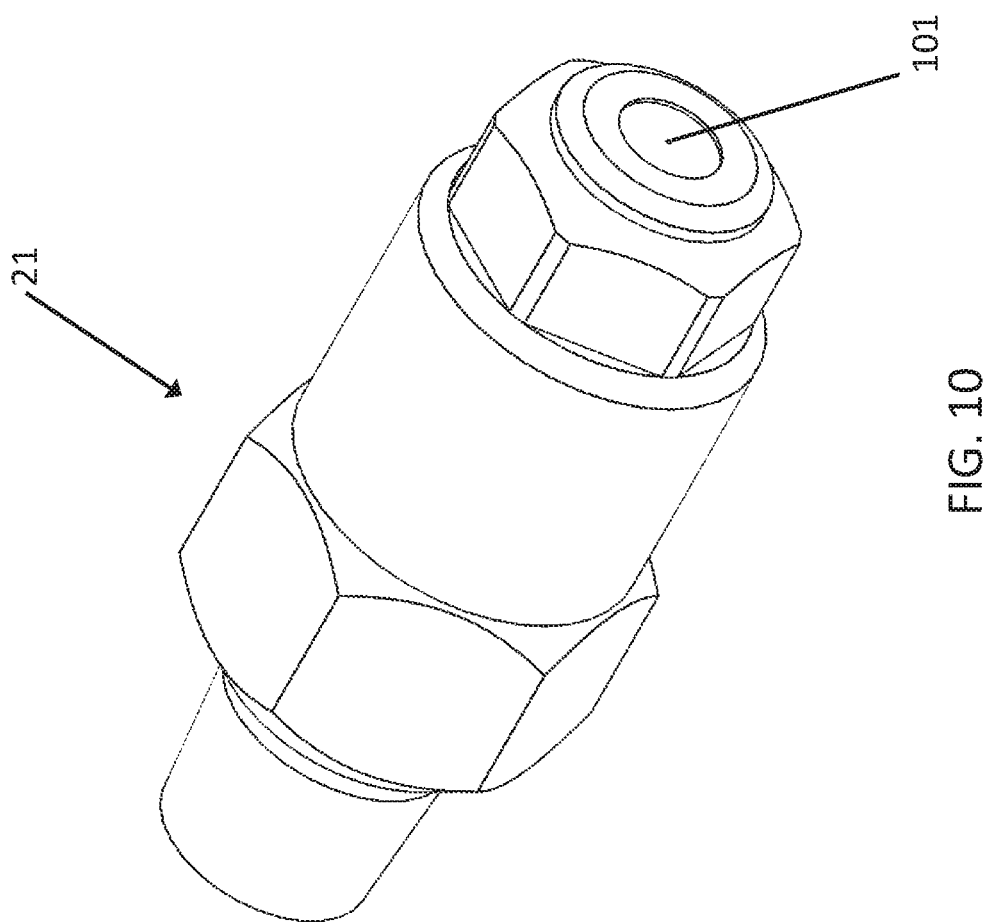
FIG. 10. A detail view of one embodiment of a hydraulic atomizing nozzle used in some embodiments of the cryochamber.

The fluid discharge orifices 21 may be any suitable orifice that is capable of atomizing the cryogenic liquid at the operating pressures of the cryogenic gas discharge system. In preferred embodiments, the fluid discharge orifices 21 are atomizing nozzles, and even more preferably, hydraulic atomizing nozzles. Examples of suitable nozzles are the "LN" and the "N" models of the Fine Spray Hydraulic Atomizing Nozzles that are commercially available from Spraying Systems Co.®. One such nozzle is depicted in FIG. 10. These models are available in brass and stainless steel, compatible with ¼ inch piping, and available in various capacities. The capacity of the nozzle depends in part on the size of the opening 101 through which the liquid is dispersed. Nozzles having a larger opening 101 generally yield a greater capacity (i.e. greater flow rate). In a preferred embodiment, the nozzles have an opening 101 with a diameter between about 0.016 inches and about 0.086 inches, and more preferably the nozzles have an opening 101 with a diameter between about 0.020 inches and about 0.076 inches. Embodiments of the nozzles may produce atomized liquids having a droplet size between about 10 microns and about 500 microns.

The fluid discharge orifices 21 may be disposed about the patient chamber as discussed in any of the embodiments above. Examples of such arrangements are shown in FIGS. 2-4, 6, and 8.

Alternatively, in some embodiments of the high pressure gas delivery system, the fluid discharge orifices 21 may be disposed about the patient chamber 12 and oriented to discharge fluid toward the middle area of the chamber 12. That is, the orifices discharge fluid in the direction of the client. Because the atomizing nozzles efficiently atomize cryogenic liquid that is delivered at a sufficiently high pressure, the nozzles in embodiments of the high pressure system discharge only atomized liquid that rapidly vaporizes. As a result, the cryogenic gases may be propelled toward the client's body without risk of burns from cryogenic liquid. This arrangement therefore further enhances the effectiveness of convection cooling discussed above.

In an exemplary embodiment, the orifices 21 are divided among at least one pair of delivery trees, and more preferably are divided among two pairs of delivery trees. Preferably, each pair of delivery trees is located adjacent to opposing walls 11, such as the front and back walls or the right and left walls. At least one orifice 21 in each delivery tree is oriented to discharge fluid in the direction of the middle area of the patient chamber 12 (or in the direction of where a client would stand). By this arrangement, cold cryogenic gases are therefore propelled at the client from multiple directions. The orifices 21 may also be strategically located at certain heights to target certain areas of a client's body where the therapeutic benefits are most desirable.

Advantageously, embodiments of the high pressure gas delivery system provide more efficient cooling of the cryotherapy chamber. In exemplary testing, embodiments consumed as little as 3.3 liters to 4.8 liters of liquid nitrogen (depending on system pressure) during a three minute cryotherapy session at a temperature of about −163° F. More particularly, in preferred embodiments, the patient chamber is maintained at a treatment temperature of about −163° F. for a period of three minutes with a consumption rate of less than or equal to about 1.5 liters of liquid nitrogen per minute, more preferably less than or equal to about 1.25 liters of liquid nitrogen per minute, and even more preferably less than or equal to about 1 liter of liquid nitrogen per minute. These consumption rates are less than the consumption rates of commercially available cryotherapy machines, which means embodiments of the improved cryochamber have lower costs of operation.

Embodiments of Gas Delivery Systems Providing Targeted Regions of Cryotherapy

In another embodiment of the gas delivery system, the plurality of fluid discharge orifices 21 are configured to concentrate the flow of cryogenic gases in particular regions of the patient chamber 12. By concentrating flow in certain regions (e.g. torso region or thigh region), the therapeutic benefits of the treatment are enhanced for certain parts of the body that now experience greater transfer of thermal heat due to increased convection cooling. For instance, in some embodiments, it is desirable to focus the cooling effects on a client's torso.

Figure 9:
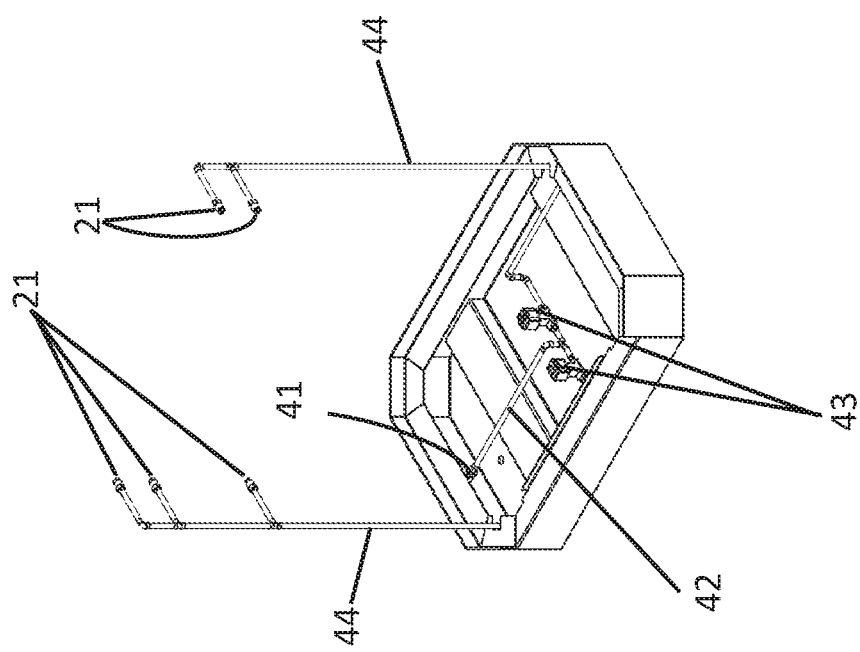
FIG. 9: A perspective view of an alternative embodiment of the cryochamber with the exterior and interior walls removed to expose the piping and five nozzles of the embodiment.

In one example of this embodiment shown in FIG. 9, the system comprises five fluid discharge orifices 21 that are distributed between two delivery trees. The first delivery tree, which may be referred to as the main delivery tree, has three orifices 21. The second delivery tree, which may be referred to as the boost delivery tree, has two orifices 21. The orifices on each delivery tree are spaced and selected to increase or decrease the flow of cryogenic fluids in certain regions of the patient chamber 12.

Preferably, the highest capacity orifice on the first delivery tree is located at a height between about 40 inches and 50 inches, and preferably around 45 inches, from the floor 14 of the patient chamber. This height corresponds approximately to the torso of a client. In a specific embodiment, this highest capacity orifice may be a size 10 "LN" or "N" hydraulic atomizing nozzle, which may have an opening with a diameter of about 0.064 inches. The middle capacity orifice on the first delivery tree may be located lower than the first orifice and at a height between about 35 inches and about 45 inches, and preferably around 40 inches, from the floor 14. This region generally corresponds with the torso or abdomen of a client. In a specific embodiment, this middle capacity orifice may be a size 4 "LN" or "N" hydraulic atomizing nozzle, which has an opening with a diameter of about 0.042 inches. The third orifice on the first delivery tree has the lowest capacity and is located below the other orifices at a height between about 23 inches and about 33 inches, and preferably around 28 inches, from the floor 14. This region generally corresponds with the thighs or waist of a client. In a specific embodiment, this lowest capacity orifice may be a size 1 "LN" or "N" hydraulic atomizing nozzle, which has an opening with a diameter of about 0.020 inches.

In the second delivery tree, the highest capacity orifice also preferably corresponds to the highest orifice. This highest capacity orifice is preferably at a height between about 35 inches and about 45 inches, and preferably around 40 inches, from the floor 14. Preferably, the highest capacity orifice of the second tree is the same type and same capacity as the highest capacity orifice on the first tree. The second orifice is preferably located at a height between about 23 inches and about 33 inches, and preferably around 28 inches, from the floor 14. This second orifice preferably corresponds to the type and capacity of the first tree's middle capacity orifice.

Advantageously, this arrangement concentrates the cooling effects in the region of the patient chamber 12 that corresponds to a client's torso. Because the orifices 21 located in this region have the highest capacity, they generate more cryogenic gas and greater velocities of the gas. The result is that the vortex or cyclonic effects are concentrated in this region, meaning that a client's body will generally experience more significant convective cooling than regions with lower levels of fluid flow. Of course, the precise arrangement may be modified so that the maximum fluid flow is concentrated in other regions of the patient chamber 12, such as the thigh region or waist region.

This arrangement may also allow for more precise control of the consumption of cryogenic liquid used to cool the patient chamber 12. In an exemplary embodiment, the main delivery tree is ordinarily active during operation of the cryochamber. The boost delivery tree, however, is selectively operable depending on the current temperature. For instance, during the initialization period or when the temperate warms above the target treatment temperature, the solenoid associated with boost delivery tree may be opened so that cryogenic liquid flows to the fluid discharge orifice on the boost delivery tree. But once the patient chamber reaches the target temperature, the solenoid may be closed, thus deactivating the boost delivery tree and reducing the system's consumption of cryogenic liquid.

Exemplary Operation of Embodiments of the Improved Cryochamber

An exemplary treatment session using embodiments of the cryochamber has a duration between about thirty seconds and about five minutes, and more preferably between about one minute and about three minutes. Depending on the purpose of the treatment and client preferences, the target temperature for the patient chamber during the treatment session in some embodiments may be between about 0° F. and about −250° F., and in other embodiments between about −50° F. and about −220° F. The cryochamber includes at least one temperature sensor disposed in the patient chamber to measure the ambient temperature of the chamber. In an exemplary embodiment, the temperature sensor is a thermocouple. The temperature sensor is preferably coupled to a control unit for the cryochamber, which controls the operation of the chamber, including the flow of cryogenic liquid to the fluid discharge orifices.

Some embodiments employ various methods to improve efficiency of the system through dynamic operation of the system's valves, regulators, and solenoids. Typically, before a treatment session that is not immediately preceded by another treatment session, the chamber is pre-cooled before starting the new treatment. For purposes of pre-cooling, the gas discharge system is preferably operated at full capacity, meaning that any valves and solenoids are completely open and that any regulator is not reducing the pressure supplied by the source. This full capacity condition is advantageous because it most rapidly cools the patient chamber. A treatment session will also often begin with the system operated a full capacity to ensure that the patient chamber is at the target temperature. Once the patient chamber is near its target temperature, such as within 15% of the target temperature, the system may then operate at a reduced capacity. In embodiments where the system comprises two or more delivery trees that are controlled by separate solenoids, the reduced capacity operation may be initiated by closing one or more (but not all) of the solenoids. Alternatively, in other embodiments, the reduced capacity may be achieved by actuating the valves to reduce the amount of liquid flowing from the cryogenic liquid source or by manipulating the regulator to reduce the operating pressure to less than the pressure at which the cryogenic liquid is stored. In embodiments were the valves, solenoids, or regulators are electrically controlled, a computer or control unit may control the operation of the cryochamber, including operation at full capacity and operation at reduced capacity mode. This reduced capacity mode thus increases the efficiency of the chamber, as it reduces the amount of cryogenic liquid consumed during the period of reduced capacity. The reduced capacity mode ordinarily continues for the remainder of the treatment unless the chamber reaches a temperature that is sufficiently warmer than the target temperature (e.g. at least 15% warmer). At that point, the full capacity mode may be re-enabled until the chamber is again sufficiently cooled.

While the foregoing specification has described specific embodiments of this invention and many details have been put forth for the purpose of illustration, it will be apparent to those skilled in the art that the invention is susceptible to additional embodiments and that certain of the details described herein can be varied considerably without departing from the basic principles of the invention.

We claim:

1. A cryotherapy chamber comprising:
   at least one wall forming a patient chamber enclosed on all sides; and
   a plurality of fluid discharge orifices disposed about said patient chamber, wherein a first and second of said orifices are positioned to discharge cryogenic fluid in a clockwise or a counter-clockwise direction about a central vertical axis of the patient chamber, wherein said first orifice is boated at a first location along the perimeter of said patient chamber and said second orifice is located at a second location along the perimeter of said patient chamber, and wherein said first location is a different lateral location along the perimeter from said second location.

2. The cryotherapy chamber of claim 1, wherein each of said first and second orifices is positioned to discharge cryogenic fluid in a direction approximately parallel to the tangent of the nearest of said at least one wall.

3. The cryotherapy chamber of claim 1, wherein each of said plurality of fluid discharge orifices is positioned to discharge cryogenic fluid in a clockwise or a counter-clockwise direction about said central vertical axis.

4. The cryotherapy chamber of claim 3, wherein each of said plurality of fluid discharge orifices is positioned to discharge cryogenic fluid in a direction approximately parallel to the tangent of the nearest of said at least one wall.

5. The cryotherapy chamber of claim 1, wherein said patient chamber has a horizontal cross section selected from the group consisting of an essentially circular shape, an essentially ovular shape, an essentially rectangular shape, and an essentially octagonal shape.

6. The cryotherapy chamber of claim 1, wherein said first location is approximately opposite of said second location.

7. The cryotherapy chamber of claim 1, wherein said first fluid discharge orifice is located at a first height in said patient chamber and has a first flow rate, wherein said second fluid discharge orifice is located at a second height in said patient chamber and has a second flow rate, and wherein said first height is different from said second height and said first flow rate is different from said second flow rate.

8. The cryotherapy chamber of claim 1, wherein said first and second fluid discharge orifices are atomizing nozzles.

9. A heaterless cryotherapy system comprising:
at least one wall forming a patient chamber;
a fluid input adapted to receive a cryogenic liquid; and
a plurality of atomizing nozzles disposed about said patient chamber and in fluid communication with said fluid input to receive a discharge fluid consisting essentially of said cryogenic liquid at a discharge pressure, wherein said plurality of atomizing nozzles are operable at said discharge pressure to discharge atomized cryogenic liquid into said patient chamber, wherein a first and second of said plurality of atomizing nozzles are positioned to discharge cryogenic fluid in a clockwise or a counter-clockwise direction about a central vertical axis of said patient chamber, wherein said first nozzle is located at a first location along the perimeter of said patient chamber and said second nozzle is located at a second location along the perimeter of said patient chamber, and wherein said first location is at a different lateral location along the perimeter from said second location.

10. The heaterless cryotherapy system of claim 9, wherein said discharge pressure is at least about 50 psi.

11. The heaterless cryotherapy system of claim 9, wherein said discharge pressure is at least about 180 psi.

12. The heaterless cryotherapy system of claim 9, wherein at least one of said plurality of atomizing nozzles is a hydraulic atomizing nozzle.

13. The heaterless cryotherapy system of claim 12, wherein each of said hydraulic atomizing nozzles has a discharge opening with a diameter between about 0.016 inches and about 0.086 inches.

14. A heaterless cryotherapy system comprising:
a cryogenic liquid source capable of supplying a discharge fluid comprising a cryogenic liquid at a supply pressure of at least about 50 psi;
at least one wall forming a patient chamber; and
a plurality of atomizing nozzles disposed about said patient chamber and in fluid communication with said source to receive said discharge fluid at a discharge pressure of at least about 50 psi, wherein said plurality of atomizing nozzles are operable to discharge atomized cryogenic liquid into said patient chamber, and wherein no fluids are added to said discharge fluid between said cryogenic liquid source and said plurality of atomizing nozzles, wherein a first and second of said plurality of atomizing nozzles are positioned to discharge said discharge fluid in a clockwise or a counter-clockwise direction about a central vertical axis of said patient chamber, wherein said first nozzle is located at a first location along the perimeter of said patient chamber and said second nozzle is located at a second location along the perimeter of said patient chamber and wherein said first location is at a different lateral location along the perimeter from said second location.

15. The heaterless cryotherapy system of claim 14, wherein said supply pressure is at least about 180 psi and said discharge pressure is at least about 80 psi.

16. The heaterless cryotherapy system of claim 14, wherein each of said atomizing nozzles are positioned to discharge atomized cryogenic liquid in a clockwise or a counter-clockwise direction about said central vertical axis of the patient chamber.

17. The heaterless cryotherapy system of claim 14, wherein each of said first and second atomizing nozzles is positioned to discharge atomized cryogenic liquid in a direction approximately parallel to the tangent of the nearest of said at least one wall.

18. The heaterless cryotherapy system of claim 14, wherein said plurality of atomizing nozzles are positioned to discharge atomized cryogenic liquid in a clockwise or a counter-clockwise direction about a central vertical axis of the patient chamber, and wherein each of said plurality of atomizing nozzles is positioned to discharge atomized cryogenic liquid in a direction approximately parallel to the tangent of the nearest of said at least one wall.

19. The cryotherapy chamber of claim 9, wherein a first atomizing nozzle is located at a first height in said patient chamber and has a first flow rate, wherein a second atomizing nozzle is located at a second height in said patient chamber and has a second flow rate, and wherein said first height is different from said second height and said first flow rate is greater than said second flow rate.

20. The cryotherapy chamber of claim 9, wherein said plurality of atomizing nozzles have a total liquid discharge rate of less than or equal to about 1.5 liters of cryogenic fluid per minute when operated at a pressure of less than or equal to 220 psi.

21. The cryotherapy chamber of claim 1, wherein said first and second orifices are positioned in approximately the same horizontal plane.

22. The cryotherapy chamber of claim 14, wherein an upper fluid discharge orifice is located at a first height in said patient chamber and has a first flow rate, wherein a lower fluid discharge orifice is located at a second height in said patient chamber and has a second flow rate, and wherein said first height is different from said second height and said first flow rate is different from said second flow rate.

23. The cryotherapy chamber of claim 14, wherein said plurality of atomizing nozzles orifices have a total liquid discharge rate of less than or equal to about 1.5 liters of cryogenic fluid per minute when operated at a pressure of less than or equal to 220 psi.

* * * * *